United States Patent [19]

Strong

[11] 3,939,218

[45] Feb. 17, 1976

[54] P-TERT-BUTYL-DIPHENYLALKANE INSECTICIDES

[75] Inventor: Jerry G. Strong, Warren, N.J.

[73] Assignee: Mobil Oil Corporation, New York, N.Y.

[22] Filed: Aug. 23, 1974

[21] Appl. No.: 499,866

[52] U.S. Cl. ...... 260/649 DD; 260/668 C; 424/354; 424/356
[51] Int. Cl.² .......................................... C07C 25/18
[58] Field of Search ................. 260/649 DD, 668 C

[56] References Cited
UNITED STATES PATENTS 2,883,428  4/1959  Nemec et al. ................ 260/649 DD Primary Examiner—D. Horwitz
Attorney, Agent, or Firm—Charles A. Huggett; Howard M. Flournoy

[57] ABSTRACT

1,1-Diphenylalkanes having a p-tert-butyl and a p'-alkyl group substituted thereon are a new class of compounds possessing a broad range of insecticidal activity.

4 Claims, No Drawings

P-TERT-BUTYL-DIPHENYLALKANE INSECTICIDES

CROSS-REFERENCE TO RELATED APPLICATIONS

Mobil Docket No. 8616 filed on the same date herewith and entitled P-Tert-Butyl-Diphenylalkane Insecticides relates to such compounds having p'-alkoxy ($C_1$–$C_4$) substitution as opposed to the p'-alkyl substitution of this application.

BACKGROUND OF THE INVENTION

This invention is directed to a new class of compounds, 1,1-diphenylalkanes having p-tert-butyl and p'-alkyl ($C_1$–$C_3$) groups, useful as insecticides. This invention is further directed to compositions comprising such compounds and an inert solid or liquid carrier and a method of using said compounds and compositions in controlling insects.

DESCRIPTION OF THE PRIOR ART

Metcalf, et al. in U.S. Pat. No. 3,787,505 (Reference 1) reported compounds having the following structure wherein R and R' are different and R is selected from the group consisting of $CH_3$, $OCH_3$, $OC_2H_5$ and $OC_3H_7$, and R' is selected from $SCH_3$ and $CH_3$:

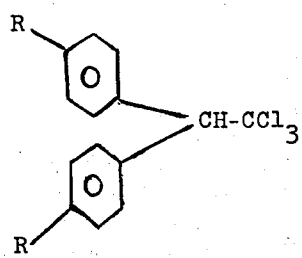

Additionally, the following compounds were reported by M. Fahmy, T. Fukuto, R. Metcalf, and R. Holmstead in *J. Agr. Food Chem.*, 21 585 (1973) (Reference 2):

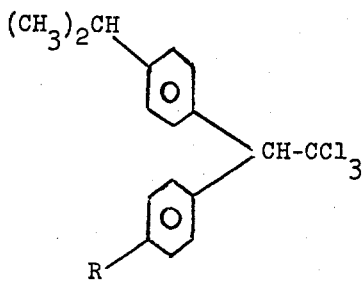

and

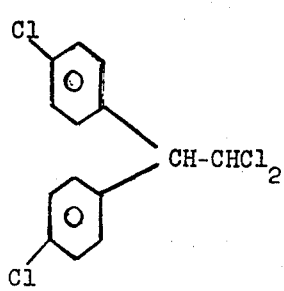

where R is $OCH_3$ and Cl.

Most of these compounds were also described by R. L. Metcalf and T. R. Fukuto, *Bull, Wld. Hlth. Org.*, 38 633 (1968) (Reference 3); compounds therein not described above include:

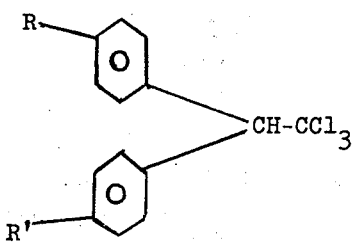

wherein R and R' are the same and are selected from Cl, $CH_3$, $C_2H_5$, $CH(CH_3)_2$, $C(CH_3)_3$, $OCH_3$ and $OC_2H_5$. The compound wherein R and R' are Cl is the insecticide DDT. The compound where R and R' and Cl and wherein $CCl_3$ is replaced by $CHCl_2$ is the insecticide DDD.

The structure-activity relationships and theories derived from such prior art (e.g. References 1, 2 and 3) strongly suggest that the compounds of the present invention should be insecticidally inactive. For example, it is stated in Reference 3, page 637 with regard to alterations of the ring substituents of DDT, "substitution of a single p-$CH_3$ for p-Cl produced a substance considerably more effective-(insecticidally)-than the isosteric DDT. However, compounds with larger alkyl groups in the p,p' positions-isopropyl, butyl, pentyl and dodecyl were completely inactive". This observation is reinforced later in the reference's summary wherein it is stated that the insecticidal activity of DDT analogs is optimal when p,p'-Cl are substituted by small relatively non-polar groups such as F, Cl, Br, $CH_3$, $OCH_3$, $C_2H_5$ and $OC_2H_5$.

A more detailed analysis of structure-activity relationships in DDT analogs presented in Reference 2 concludes that for maximum activity the overall size of the molecule is critical and deviation from the size of the DDT molecule results in reduced activity.

Accordingly, one would conclude from this that any DDT analogs bearing the large p-tert-butyl group such as the compounds of the present invention, all of which are thus much larger than DDT, would be insecticidally inactive.

The insecticide screening data presented below clearly shows that this is not the case. Thus, the activity of the new compounds is surprising and could not be predicted by currently held theories of insecticidal structure and activity relationships.

SUMMARY OF THE INVENTION

This invention provides new 1,1-diphenylalkanes wherein the phenyl groups are substituted at the para position, one by tert-butyl and the other by alkyl substituents. These new compounds are highly effective in combating various insect classes including lepidoptera, e.g. southern armyworm, and coleoptera, e.g. Mexican bean beetle. These two classes of insects represent the largest group of insect pests in terms of the annual damage they inflict on crops.

The compounds embodied in this invention have the following general structure:

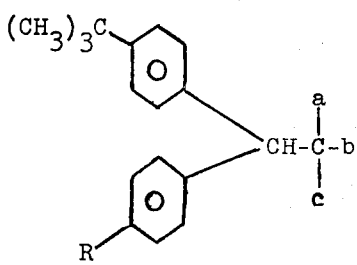

wherein R is alkyl ($C_1$ to $C_3$) i.e. selected from the group consisting of $CH_3$, $C_2H_5$ and $C_3H_7$, and a, b and c are selected from the group consisting of hydrogen, chloro and alkyl ($C_1$–$C_2$), i.e. $CH_3$ and $C_2H_5$.

The compounds of the present invention, unlike DDT and DDD, are expected to be biodegradable and non-persistent in the environment. R. L. Metcalf, et al. report in the *Bull. Wld. Hlth. Org.*, 44, 363 (1971) that DDT analogs having substituent groups (e.g. alkoxy and alkyl) readily attached by multifunction oxidase enzymes present in the environment undergo substantial biological degradation and do not appear to be readily stored or concentrated in animal tissues or food chains. Furthermore, as pointed out by I. P. Kapoor, et al. *J. Agr. Food Chem.*, 21, 310 (1973), a single biodegradable substituent is sufficient to impart a substantial degree of biodegradability to the compound.

NON-LIMITING EXAMPLES 1-(p-tert-Butylphenyl)-1-(p′-ethylphenyl)ethane;
1-(p-tert-Butylphenyl-1-(p′-ethylphenyl)propane;
1-(p-tert-Butylphenyl)-1-(p′-methylphenyl)-2-chloropropane;
1-(p-tert-Butylphenyl)-1-(p′-methylphenyl)-2,2-dichloroethane;
1-(p-tert-Butylphenyl)-1-(p′-methylphenyl-2,2,2-trichloroethane;
1-(p-tert-Butylphenyl)-1-(p′-ethylphenyl)-2,2,2-trichloroethane;
1-(p-tert-Butylphenyl)-1-(p′-ethylphenyl)-2-methylpropane;
1-(p-tert-Butylphenyl)-1-(p′-methylphenyl)-2-methylpropane;
1-(p-tert-Butylphenyl)-1-(p′-ethylphenyl)-2-2, -dimethylpropane, etc.

In general, the compounds of this invention are prepared by condensing tert-butylbenzene with an appropriate substituted carboxylic acid chloride and/or chloral in the presence of a suitable catalyst, e.g. aluminum chloride.

The resulting ketones are reduced to the corresponding alcohols using the convenient RED-AL™ reducing reagent available from Aldrich Chemical Company.

The purified alcohols are then condensed with an appropriate alkylbenzene in the presence of sulfuric acid. A solvent such as dichloromethane, ethylene chloride or acetic acid may be employed or excess alkylbenzene may serve as solvent.

The starting materials - - - tert-butylbenzene, carboxylic acid chlorides, and alkylbenzenes are articles of commerce.

EXAMPLE 1

4′-tert-Butyl-2,2-dichloroacetophenone

A solution of 74g (0.5 mole) of dichloroacetyl chloride and 67g (0.5 mole) of tert-butylbenzene was added over 0.5 hr. at 0–5°C to a vigorously stirred mixture of 68g (0.5 mole) of aluminum chloride and 75 ml of carbon disulfide. The reaction mixture was stirred for 4 hrs. while the temperature rose to ambient and then poured onto a mixture of 500 ml of ice and 100 ml of 12M HCl. The organic products were extracted into ethyl ether (2 × 400 ml) and the ethereal solution was washed with dil HCl, water, aqueous bicarbonate with brine, dried over magnesium sulfate and concentrated. Obtained was 120g of dark liquid which crystallized from cold (−40°C) 30–60 pet ether to provide 70g of a white solid after several washings with cold pet ether; mp 47°–49°C: ir (KBr) 3.4 (m), 5.9 (s), 6.3 (s), 11.7 (s), 12.6 (s); nmr ($CDCl_3$) 6.7 (1H, s) ppm.

EXAMPLE 2

1-p-tert-Butylphenyl-2,2-dichloroethanol

A 50 ml portion (0.2 mole) of a 70% RED-AL solution (Aldrich Chemical Company) was added over 0.5 hr. to a solution of 49g (0.2 mole) of Example 1 in 300 ml of benzene. Dry nitrogen blanketed the reaction surface and the temperature was controlled at 20°–30°C. After stirring for 2 hrs. at ambient, the solution was cooled to 10°C. and the excess reducing agent was neutralized by the drop-wise addition of 30 ml of 20% sulfuric acid. The white solid which separated was filtered and washed with benzene and the benzene filtrates were concentrated to afford 50g of a clear liquid. A 38g portion was distilled via short path to provides 35g of a clear, colorless liquid; Bp 112°–118°C (0.5 mm); ir (film) 2.9 (s), 3.4 (s), 11.8 (s), 12.7 (s) microns; nmr ($CDCl_3$) 7.23 (4H, m), 5.65 (1H, d) 4.78 (1H, d) 3.40 (1H, s), 1.25 (9H, s) ppm.

EXAMPLE 3

1-p-tert-Butylpenyl-1-p′-ethylphenyl-2,2-dichloroethane

A mixture of 16.2g (0.15 mole) of ethylbenzene and 17 ml of 96% sulfuric acid was prepared at 0°–5°C and to this was added over 15 min. at 0°–5°C a solution of 6.3 g (0.026 mole) of Example 2 in 9 ml of dichloromethane. The mixture was vigorously stirred for 2 hrs. while the temperature rose to ambient and then poured onto 100 ml of crushed ice. The organic products were extracted into ethyl ether and the ethereal solution was washed with water, aqueous bicarbonate and with brine, dried over magnesium sulfate and concentrated on the steam bath at 1.0 mm. Obtained following recrystallization of the concentrate from hexane was 5.1g of white solid: mp 110.5–112; ir (KBr) 3.5 (s), 6.7 (m), 9.8 (m), 13.3 (s) microns; nmr ($CDCl_3$) 7.3–7.1 (8H, m), 6.31 (1H, d) 4.48 (1H, d) 2.60 (2H, q), 1.22 (9H, s), 1.18 (3H, t) ppm. A VPC analysis indicated 100% p,p′-isomer.

EXAMPLE 4

4′-tert-Butylbutyrophenone

The procedure of Example 1 was followed for the reaction of 53g (0.5 mole) of bytyryl chloride with 67g (0.5 mole) of tert-butylbenzene. Obtained after high vacuum concentration was 94g of a clear liquid. VPC indicated a pure product. Ir (film) 3.5 (s), 5.9 (s) microns; nmr (CDCl$_3$) 7.65 (4H, center of doublet of doublets, 2.9 (2H, t), 1.75 (2H, sextet), 1.3 (9H, s), 0.95 (3H, t) ppm.

EXAMPLE 5

4'-tert-Butyl-2-chlorobutyrophenone

To a solution of 51g (0.25 mole) of Example 4 in 200 ml of carbontetrachloride was added portionwise 38g (0.28 mole) of sulfuryl chloride and the reaction solution was heated to 70°C for 1.5 hr. The solution was then washed with water, aqueous bicarbonate and with brine, dried over magnesium sulfate and concentrated. Obtained was 56g of a liquid which was distilled to afford 33g of a center fraction of clear, colorless product: Bp 113°–118° (0.4 mm); ir (film) 3.4 (m), 5.9 (s), 6.3 (m), 7.8 (m), 11.7 (m), microns; nmr (CDCl$_3$) 7.67 (4H, d of d), 5.03 (1H, t), 2.04 (2H, quintet), 1.28 (9H, s), 1.11 (3H, t) ppm.

EXAMPLE 6

1-(p-tert-Butylphenyl)-2-chlorobutanol

The procedure of Example 2 was followed for the reaction of 35.7g (0.15 mole) of Example 5 with 37.5 ml (0.15 mole) of RED-AL. Obtained was 32.5g of a liquid product which was distilled to afford 26.7g of a colorless liquid: Bp 112°–118°C (0.5 mm); ir (film) 2.9 (m), 3.4 (s), 6.9 (m), 11.9 (m), microns; nmr (CDCl$_3$) 7.28 (4H, d of d), 4.70 (1H, d of d), 4.02 (1H, m), 2.70 (1H, broad), 1.65 (2H, m), 1.25 (9H, s), 0.95 (3H, t) ppm.

EXAMPLE 7

1-p-tert-Butylphenyl-1-p-ethylphenyl-2-chlorobutane

The procedure of Example 3 was followed for the reaction of 19.1g (0.18 mole) of ethylbenzene with 7.2g (0.03 mole) of Example 6 in 10 ml of dichloromethane and 20 ml of 96% sulfuric acid. Obtained was 8.5g of a clear, amber liquid product: ir (film) 3.4 (s), 6.7 (m), 6.8 (m), 12.3 (m), 12.7 (m) microns; nmr (CDCl$_3$) 7.50–6.90 (8H, m), 4.56 (1H, m) 4.05 (1H, d), 2.52 (2H, q), 1.60 (2H, m), 1.27 (3H, t), 1.18 (9H, s), 10.5 (3H, t) ppm. A VPC analysis indicated 90% p,p'-isomer, 5% o,p'-isomer, 5% other products.

EXAMPLE 8

1-p-tert-Butylphenyl-1-p'-methylphenyl-2-chlorobutane

The procedure of Example 3 was followed for the reaction of 12.6g (0.14 mole) of toluene with 5.5g (0.02 mole) of Example 6 in 8 ml of dichloromethane and 15 ml of sulfuric acid. Obtained was 4.4g of a clear, yellow liquid product: ir (film) 3.4 (s), 6.7 (s), 6.8 (m), 7.3 (m), 12.6 (m), 12.8 (s) microns; nmr (CDCl$_3$) 7.35–6.95 (8H, m), 4.55 (1H, m), 4.03 (1H, d), 2.20 (3H, s), 1.18 (9H, s), 1.00 (3H, t) ppm. A VPC analysis indicated a product mixture of 90% p,p'-isomer, 5% o,p'-isomer and 5% other products.

EXAMPLE 9

4'-tert-Butyl-2-chloropropiophenone

The procedure of Example 1 was followed for the reaction of 63.5g (0.5 mole) of 2-chloropropionyl chloride with 67g (0.5 mole) of tert-butylbenzene. Obtained after high vacuum concentration was 100g of a clear, yellow liquid product: ir (film) 3.4 (s), 5.9 (s), 6.3 (s), 8.0 (s), 10.5 (s), 11.8 (s) microns: nmr (CDCl$_3$) 7.67 (4H, d of d), 5.21 (1H, q), 1.67 (3H, d), 1.28 (9H, s) ppm. A VPC analysis indicated one pure product.

EXAMPLE 10

1-p-tert-Butylphenyl-2-chloropropanol

The procedure of Example 2 was followed for the reaction of 67.4g (0.3 mole) of Example 9 with 75 ml of RED-AL in 400 ml of benzene. Obtained following vacuum concentration was 69g of a clear liquid which was distilled to afford 53g of clear, colorless liquid product: Bp 100°–102° (0.2 mm); ir (film) 2.9 (s), 3.4 (s) 6.9 (m), 7.3 (m), 9.1 (m), 9.7 (m), 10.0 (m), 11.9 (m) microns. A VPC analysis indicated one pure product.

EXAMPLE 11

1-p-tert-Butylphenyl-1-p'-ethylphenyl-2-chloropropane

The procedure of Example 3 was followed for the reaction of 6.8g (0.03 mole) of Example 10 with 19g (0.18 mole) of ethylbenzene in 10 ml of dichloromethane and 20 ml of sulfuric acid. Obtained following recrystallization of the work-up residue from 20–40 pet ether was 4.7g of a white, crystalline product: mp 71°–75°C; ir (CCl$_4$), 3.4 (s), 7.9 (m), 9.9 (m), 15.1 (s), 15.3 (m) microns; nmr (CDCl$_3$) 7.4–7.0 (8H, m), 4.72 (1H, m), 3.97 (1H, d), 2.58 (2H, q), 1.43 (3H, d), 1.30 (3H, t), 1.21 (9H, s) ppm. A VPC analysis indicated a product purity of 95%.

EXAMPLE 12

The new p-tert-butyl-1,1-diphenylalkanes of this invention were evaluated in standard greenhouse insecticide tests using housefly (HF, bait test), Mexican bean beetle (MB), southern armyworm (SA) and yellow fever mosquito larvae (YF). The rates of application were 500, 100, 10 and 1 ppm of active ingredient (p,p'-isomer). The known compounds methyl methoxychlor, methyl ethoxychlor, methoxychlor and DDT were included for comparisons in these tests. According to references 1, 2 and 3, these are the most broadly effective of the known insecticidal DDT analogs. The results as set forth below indicate the percent control of each insect species.

| COMPOUND | RATE (PPM) | HF | MB | SA | YF |
|---|---|---|---|---|---|
| Example 3 | 500 | 90 | 90 | 20 | — |
|  | 100 | 20 | 10 | — | — |
|  | 10 | — | — | — | 100 |
|  | 1 | — | — | — | 80 |
| Example 7 | 500 | 10 | 70 | 30 | — |
|  | 100 | — | 10 | — | — |
|  | 10 | — | — | — | 80 |
|  | 1 | — | — | — | 20 |
| Example 8 | 500 | 70 | 50 | 20 | — |
|  | 100 | 10 | 20 | — | — |
|  | 10 | — | — | — | 60 |
|  | 1 | — | — | — | 10 |
| Example 11 | 500 | 80 | 100 | 10 | — |
|  | 100 | 30 | 10 | 10 | — |
|  | 10 | — | — | — | 80 |
|  | 1 | — | — | — | 40 |
| Methyl Methoxychlor | 500 | 100 | 100 | 10 | — |
|  | 100 | 90 | 80 | — | — |
|  | 10 | — | — | — | 100 |
|  | 1 | — | — | — | 100 |
| Methyl Ethoxychlor | 500 | 90 | 100 | 20 | — |
|  | 100 | 20 | 100 | — | — |
|  | 10 | — | 30 | — | 100 |

-continued

| COMPOUND | RATE (PPM) | HF | MB | SA | YF |
|---|---|---|---|---|---|
| | 1 | — | — | — | 100 |
| Methoxychlor | 500 | 100 | 100 | 10 | — |
| | 100 | 90 | 100 | — | — |
| | 10 | — | — | — | 100 |
| | 1 | — | — | — | 100 |
| DDT | 500 | 100 | 40 | 100 | — |
| | 100 | 100 | 10 | 60 | — |
| | 10 | — | — | — | 100 |
| | 1 | — | — | — | 100 |

Test Methods

House Fly; 1 milliliter of an aqueous solution or suspension of the test compound was pipeted into a 9 cm. petri dish containing filter paper and 0.1 gram of granular sugar. Ten adult house flies were admitted and the dish closed. Observations were made periodically for knockdown and at 24 hours for mortality.

Southern armyworm and Mexican Bean Beetle; lima bean leaves of uniform size were momentarily dipped in a water-acetone solution of the test compound and the treated leaves were then placed on moistened filter paper in 9 cm. petri dishes and allowed to air dry. When dry, five, third, or fourth instar larvae were introduced and encouraged to feed on the treated foliage by means of confinement. The dishes were closed and held for observation of mortality and feeding during a 48 to 72 hour period.

Early fourth stage mosquito larvae are exposed to solutions, emulsions or suspensions of the materials in water. The compounds are dissolved in acetone and added to the water; water-soluble compounds remain in solution and the others become finely divided suspensions. Compounds are screened initially at 10 ppm using approximately 5 larvae per 100 ml of treated water. Each treatment is replicated twice.

From the data presented in Example 12, it is noted that contrary to currently held theories of structure-activity relationships in DDT analogs, the compounds of the present invention are effective insecticides on a broad range of insect species.

Although the present invention has been described with the preferred embodiments, it is to be understood that modifications and variations may be resorted to without departing from the spirit and scope of the invention as one skilled in the art will readily understand.

I claim:

1. A compound having the following general structure:

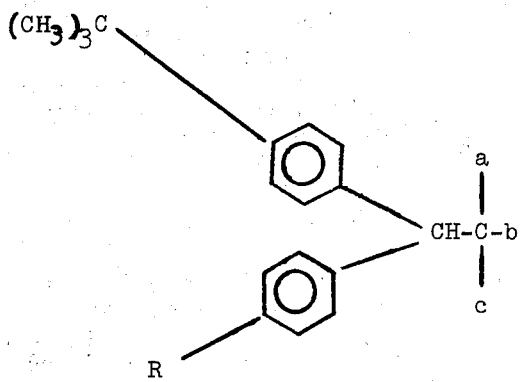

wherein R is selected from the group consisting of $CH_3$ and $C_2H_5$, a is chloro, b is selected from the group consisting of $CH_3$ and $C_2H_5$ and c is hydrogen.

2. The compound of claim 1 wherein R is $C_2H_5$, a is chloro, b is $C_2H_5$ and c is hydrogen.

3. The compound of claim 1 wherein R is $CH_3$, a is chloro, b is $C_2H_5$ and c is hydrogen.

4. The compound of claim 1 wherein R is $C_2H_5$, a is chloro, b is $CH_3$ and c is hydrogen.

* * * * *